Feb. 11, 1958 F. M. SCHWAB Plant Pat. 1,681
SEEDLESS GRAPE
Filed Nov. 2, 1956
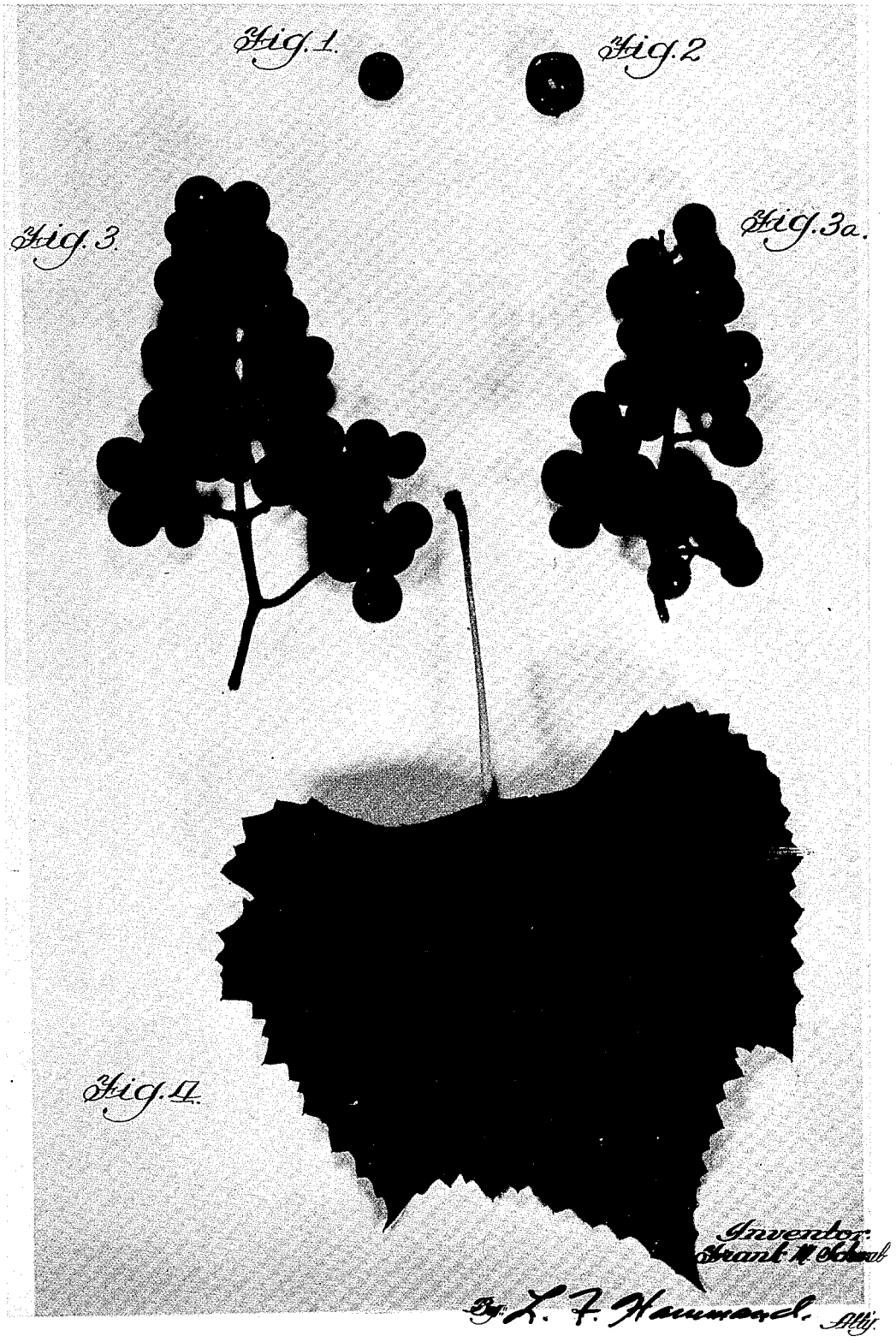

United States Patent Office

Plant Pat. 1,681
Patented Feb. 11, 1958

1,681

SEEDLESS GRAPE

Frank M. Schwab, Mankato, Minn.

Application November 2, 1956, Serial No. 620,160

1 Claim. (Cl. 47—62)

My invention relates to a new and distinct variety of grape plant. The original plant of this new variety was discovered by me as a seedling on my farm in Mankato township, Minnesota; which seedling developed from a seed resulting from the open-pollination of an unknown variety of grape planted by me at an earlier date.

Since my discovery of the original plant, I have asexually reproduced a large number of plants from the original mother plant, by layers and cuttings, on my said farm.

My object in the asexual propagation of the unique, original mother plant was to determine the characteristics of the plant and of its fruit by the testing of a large number of plants. The distinguishing features of my new variety have proved to be permanent. The plant has proved itself to have unusual commercial possibilities because of its productivity and hardiness; and because of the sweetness and high flavor of its fruit, the tender skin and flesh, and particularly the seedlessness of its fruit.

In the accompanying drawings:

Figure 1 shows a typical central longitudinal section of a berry of my new variety exhibiting very small, undeveloped seeds;

Figure 2, by contrast, shows a similar section of a berry of the Concord variety, unpatented, showing its typical fullsized seeds;

Figures 3 and 3*a* illustrate two typical clusters of fruit, one with a shoulder and one without; and Figure 4 shows a typical leaf in full color.

In general, the distinct and new variety of grape plant, which is the subject of my invention and discovery, is characterized primarily by the seedlessness of its fruit; and also by its productivity and hardiness. The fruit is also characterized by its sweetness and high flavor, and its tender skin and flesh. These characteristics I now refer to in greater detail.

Under the conditions at Mankato, Minnesota, about 45° north latitude, my new variety of plant is high in productivity producing as many clusters of fruit as Concord or even more. The plant is as vigorous as Concord; and is hardier than Concord.

The leaves of the plant are medium to large in size, thick, medium green in color, slightly glossy, relatively smooth on the upper surface, gray to light bronze in the lower surface. The leaves are generally similar to Concord in appearance.

At Mankato, Minnesota, my new variety of grape plant begins to mature its fruit in midseason, about with Concord. Its harvesting period is about three to four weeks in length.

The fruit clusters are medium in size and usually single-shouldered or not shouldered. The non-shouldered clusters are long and cylindrical, normally loose, but sometimes fairly compact. Each cluster generally contains several small, undeveloped berries. The berries do not shatter even when fully ripe as in some varieties Under the conditions existing where I have reproduced and tested my new variety of grape plant, the berries are medium in size, but not uniform in size. Some of the berries in a cluster are quite small, the size of Concord Seedless; and some large, the size of Concord. In general, the single grape is smaller than Concord, larger than Delaware, unpatented, and much larger than Concord Seedless. The berries, like those of Concord, are roundish in shape, blue-black in color, and covered with abundant bloom.

The pistils of the flowers apparently are normal. Non-viable pollen is produced on semi-erect stamens.

The skin of the berry is thinner and more tender than that of Concord and is slightly adherent to the flesh. The flesh is more tender, sweeter, and considerably higher in flavor than Concord; and is less astringent. The fruit, as a whole, is sweet and high in flavor; more so than that of Concord, and is the highest flavored grape known to me.

Since the discovery of this plant, only incipient seeds have been found upon examination of the fruit each year at Mankato, Minnesota. Only very small, undeveloped seeds have been present. Up to 50 varieties of bearing grapes have been grown within 500 feet, and up to 11 varieties of grapes have been grown within ten feet of my new variety. Therefore, the reason for the seedlessness of my new variety is not poor pollination. This seedlessness is a distinguishing feature, which has proved to be permanent.

The grape above described, and the plant producing it, of course, may vary in slight details depending upon climatic, weather, and soil conditions.

What I claim is:

A new and distinct variety grape plant substantially as herein shown and described, characterized by its seedless fruit; the productivity and hardiness of the plant; and the sweetness, high flavor, and tender skin and flesh of its fruit.

No references cited.